US011338034B2

(12) United States Patent
Rouquet et al.

(10) Patent No.: US 11,338,034 B2
(45) Date of Patent: May 24, 2022

(54) HYDROXYAPATITE POWDER AND PROCESS FOR PRODUCING SAME, COMPOSITION BASED ON THIS POWDER AND PROCESS FOR PREPARING SAME AND KIT COMPRISING THIS POWDER

(71) Applicant: URODELIA, Saiguede (FR)

(72) Inventors: Nicole Rouquet, Toulouse (FR); Patrick Frayssinet, Saint-lys (FR)

(73) Assignee: URODELIA, Saiguede (FR)

( * ) Notice: Subject to any disclaimer, the term of this patent is extended or adjusted under 35 U.S.C. 154(b) by 1955 days.

(21) Appl. No.: 14/891,476

(22) PCT Filed: Mar. 4, 2014

(86) PCT No.: PCT/FR2014/050478
§ 371 (c)(1),
(2) Date: Jan. 25, 2016

(87) PCT Pub. No.: WO2014/184453
PCT Pub. Date: Nov. 20, 2014

(65) Prior Publication Data
US 2021/0308259 A1  Oct. 7, 2021

(30) Foreign Application Priority Data
May 15, 2013  (FR) ..................... 1354361

(51) Int. Cl.
| *A61K 9/00* | (2006.01) |
| *A61K 35/00* | (2006.01) |
| *A61K 39/00* | (2006.01) |
| *A61K 39/385* | (2006.01) |
| *C01B 25/32* | (2006.01) |
| *A61P 35/00* | (2006.01) |
| *B01J 20/04* | (2006.01) |
| *B01J 20/28* | (2006.01) |
| *B01J 20/30* | (2006.01) |

(52) U.S. Cl.
CPC .......... *A61K 39/385* (2013.01); *A61K 9/0019* (2013.01); *A61K 39/001176* (2018.08); *A61P 35/00* (2018.01); *C01B 25/325* (2013.01); *A61K 2039/54* (2013.01); *A61K 2039/55505* (2013.01); *A61K 2039/804* (2018.08)

(58) Field of Classification Search
None
See application file for complete search history.

(56) References Cited

FOREIGN PATENT DOCUMENTS

| EP | 0337123 | 10/1989 |
| GB | 2487864 | 8/2012 |
| WO | 2006/122914 | 11/2006 |

OTHER PUBLICATIONS

Izykowska et al (J. Hematol. Oncol. 2020, 13, 176: 1-38) (Year: 2020).*
Kerkar and Restifo (Cancer Res.2012, 72(13): 3125-3130) (Year: 2012).*
Beatty and Gladney (Clin. Canc. Res. 2014, 21(4): 687-692) (Year: 2014).*
Spranger, S (Int. Immunol. 2015, 28(8): 383-391) (Year: 2015).*
Kalos and June (Immunity, 2013, 39: 49-60) (Year: 2013).*
Berger et al (Int. J. Cancer. 111: 229-237, 2004) (Year: 2004).*
Schumacher and Schrieber (Science, 2015, 384 (6230): 69-74) (Year: 2015).*
International Search Report in PCT/FR2014/050478 dated Aug. 6, 2014.
I-Ming Hung et al., "The Properties of Sintered Calcium Phosphate with [Ca]/[P] = 1.50," Int. J. Mol. Scie., 13(10):13569-13586 (2012) XP055101424.
Ciocca et al., "A pilot study with a therapeutic vaccine based on hydroxyapatite ceramic particles and self-antigens in cancer patients," Cell Stress and Chaperones, 12(1):33-43 (2007) XP055131849.

* cited by examiner

*Primary Examiner* — G. R. Ewoldt
*Assistant Examiner* — Marianne Dibrino
(74) *Attorney, Agent, or Firm* — Morgan, Lewis & Bockius LLP

(57) ABSTRACT

The present invention relates to a hydroxyapatite and/or tricalcium phosphate powder characterized in that it has undergone at least one sintering step at a temperature between 400° C. and 600° C. The invention also relates to a process for preparing such a powder, and to a composition comprising such a powder for use as an anti-tumour autovaccine and particularly in the treatment of the following pathological conditions: osteosarcoma, B or T lymphoma, mammary tumour, melanoma, haemangiosarcoma, mastocytoma, fibrosarcoma, brain tumours and schwannoma in a subject. The present invention also covers a drug combination comprising the composition of the invention and at least one second therapeutic agent, preferably an anti-tumour agent and/or a radiotherapeutic agent.

9 Claims, 7 Drawing Sheets

Figure 7

| semaine | | | | | |
|---|---|---|---|---|---|
| 1 | Asp | | | | |
| 2 | | Vinc | Cyclo | | |
| 3 | | Vinc | | | |
| X4 | | Vinc | | | |
| X5 | | | | | |
| X6 | | | | | |
| X7 | | | | Adri | |
| 8 | | | | | |
| 9 | | | | | |
| 10 | | | | Lomu | |
| 11 | | | | | |
| X12 | | | | | |
| 13 | | Vinc | Cyclo | | |
| 14 | | | | | |
| 15 | | | | | |
| X16 | | | | Adri | |
| 17 | | | | | |
| 18 | | | | | |
| 19 | | | | Lomu | |
| X20 | | | | | |
| 21 | | | | | |
| 22 | | | | | |
| 23 | | | | | |
| X24 | | | | | |

HYDROXYAPATITE POWDER AND PROCESS FOR PRODUCING SAME, COMPOSITION BASED ON THIS POWDER AND PROCESS FOR PREPARING SAME AND KIT COMPRISING THIS POWDER

RELATED APPLICATIONS

The present application is filed pursuant to 35 U.S.C. 371 as a U.S. National Phase application of International Patent Application No. PCT/FR2014/050478, which was filed Mar. 4, 2014, claiming the benefit of priority to French Patent Application No. 1354361, which was filed on May 15, 2013. The entire text of the aforementioned applications is incorporated herein by reference in its entirety.

FIELD OF APPLICATION

The field of the invention is that of immunotherapy treatments, in particular cancer treatments.

More specifically, the invention relates to autologous treatments by immunostimulation.

More specifically still, the invention relates to means for combating cancer, comprising antitumor drugs, preferably vaccines, obtained from the tumor antigens of patients.

The present invention targets in particular a drug, for example an antitumor vaccine, based on hydroxyapatite and/or on tricalcium phosphate.

The invention also relates to a process for preparing a hydroxyapatite and/or tricalcium phosphate powder with a view to use thereof as a drug, to a process for preparing the drug based on the hydroxyapatite and/or tricalcium phosphate powder and also to a treatment kit comprising the hydroxyapatite and/or tricalcium phosphate powder.

PRIOR ART

It is well known that there are several forms of treatment against cancer by immunotherapy:
  the administration of pharmacological substances (such as interleukin or interferon) which non-specifically increase the immune response. These therapies have a variable degree of toxicity and, although they can show a certain efficacy, many patients treated in this way respond weakly. These therapies cause an amplification of numerous immune functions;
  the use of specific antibodies against the tumor antigens present at the surface of tumor cells. These antibodies are generally humanized hybrid antibodies. However, the efficacy of these treatments is limited owing to the antigenic variability of tumor cells, since certain tumor cells, at the time of diagnosis, express the antigens of interest and others do not;
  T cell stimulation. This form of therapy is in keeping with the subject of the invention. T cell stimulation can be:
    adoptive (sample of antitumor T cells taken, in vitro increase in the number thereof, then administration to the patient), or
    active (tumor antigens brought into contact in vitro or in vivo, with macrophages or related cells so that the antigen-presenting cells (APCs) stimulate the T lymphocytes). These agents which stimulate T lymphocytes are likened to therapeutic vaccines.

There are several strategies for generating vaccines which stimulate the T system in active and specific form. One of these immunotherapy strategies is based on the use of heat shock proteins as an adjuvant. The function of an adjuvant is to cause the immune system to react to a molecule to which it would not necessarily react or at least not at the doses used. It triggers a reaction to the foreign body, bringing a large number of antigen-presenting cells (APCs) to the injection site which will then provide the lymphocyte lines with information regarding the molecules that they must identify and eliminate. This information is provided by exposing the molecules, against which immunization is to take place, on the surface of the APCs and by the synthesis, by said APCs, of various cytokines and interleukins and also membrane co-factors. Thus, in order to generate vaccines which stimulate the T system via heat shock proteins as an adjuvant, heat shock proteins (HSPs) such as gp 96 or HSP 70 are extracted from the tumor. These proteins are chaperones and become linked to numerous peptides, including the peptides (antigens) specific for the tumor of each patient. They thus constitute a molecular fingerprint of the tumor to be eradicated and differ from one patient to another and from one tumor to another. For the same patient, it also varies during the development of the tumor owing to the genetic instability of cancer cells.

This strategy means that the vaccinating proteins must be purified from each tumor against which they must immunize the patient. The purification protocol is long, difficult to industrialize and subject to multiple contaminations by endotoxins. It is standard practice to purify HSPs from ground tumor material which is subjected to a series of centrifugation, precipitation, chromatography on Con A, electrophoretic analysis, and chromatography on Mono Q FPLC.

U.S. Pat. Nos. 6,447,781, 6,436,404, 6,410,028, 6,383, 494 and 6,030,618 describe methods for purifying HSP proteins which consist in using Con A Sepharose chromatographic columns. However, these methods can be improved.

Moreover, since the studies by Tizelius in 1973, it has been known that hydroxyapatite (HAP) particles can be used to purify proteins from complex solutions. HAP powders are used as a fixed bed in chromatography columns through which the solution containing the molecule(s) to be purified is percolated. These molecules bind to the surface of the HAP powder particles, from where they are desorbed using various concentrations of saline solutions such as phosphate buffers or else sodium chloride, or calcium chloride, thereby making it possible to separate the various molecules from the solution using gradients of phosphate buffers or the like.

Patent application WO 2006/122914 describes the capacity of these HAP particles to purify heat shock proteins from tissue extracts. As stated above, the purification of heat shock proteins from a tumor biopsy makes it possible to have tumor-specific peptides and proteins. These peptides and proteins vary not only from one patient to another, but also throughout the development of the tumor in the same individual owing to the genetic instability of the cancer cell. WO 2006/122914 describes more particularly a process for preparing tumor antigens in a single step, said process being intended to produce them in a form recognizable by the immune system, so that it can be applied on a large scale by personnel who are not qualified biochemists. It is also known from this international patent application that powders of HAP and also of other calcium salts can thus be used as vaccination adjuvants and that hydroxyapatite powder which has adsorbed the tumor antigens specific for a tumor can be used as a drug against said tumor. Thus, the same HAP powder can be used both to purify the proteins specific for a tumor and to stimulate the immune system against these proteins when powders and proteins are injected together. However, the processes for preparing the HAP powders and the powders themselves can be improved.

The use of powders for this purpose has many constraints.

The powders must have a large specific surface area in order to bind a large amount of protein.

They must have a high flowability in order to be able to be injected using injection needles and must have sufficient resistance so as not to clog chromatography columns. Furthermore, they must not clog when a solution of proteins also containing fibrin which polymerizes with calcium (present in HAP) is percolated through said chromatography column.

In addition to these mechanical constraints, the specific surface properties must allow the binding of proteins, in particular heat shock proteins and even more particularly gp96 and Hsp70. Finally, the powders which have bound the proteins specific for a given tumor, particularly heat shock proteins, must not, after injection, cause any bothersome tissue reactions, nor any systemic side effect.

BRIEF DESCRIPTION OF THE INVENTION

In order to achieve these improvement objectives, the inventors have, to their credit, developed an improved process for producing a hydroxyapatite and/or tricalcium phosphate powder.

The present invention therefore relates, firstly, to a hydroxyapatite and/or tricalcium phosphate powder, characterized in that it has undergone at least one sintering step at a temperature of between 400° C. and 600° C.

The invention also relates to an HAP and/or tricalcium phosphate powder which has undergone at least one sintering step at a temperature of between 400° C. and 600° C. and which exhibits at least one of the following particular fundamental criteria such as:
 the particle size G of the powder is ≤200 μm, preferably 0<G≤25 μm or between 25 μm and 45 μm,
 the specific surface area SS of the powder is ≥30 m²/g,
 a percentage ratio of the width at half maximum to total height of the line, on an X-ray diffraction spectrum, with an angle 2θ value equal to approximately 31.773 degrees+/−1%, of between 0.2% and 0.35%, preferably equal to 0.3%+/−10%.

The invention also relates to an HAP and/or tricalcium phosphate powder which has at least one of the following characteristics:
 a particle size G such that G≤200 μm, preferably 0<G≤25 μm or between 25 μm and 45 μm,
 a specific surface area SS such that SS≥30 m²/g,
 a ratio of the width at half maximum to total height of the line on an X-ray diffraction spectrum, with an angle 2θ value equal to approximately 31.773 degrees+/−1%, reported as percentage, of between 0.2% and 0.35%, preferably equal to 0.3%+/−10%.

The invention also relates to a process for producing a hydroxyapatite and/or tricalcium phosphate powder, characterized in that it comprises at least one step of sintering a hydroxyapatite and/or tricalcium phosphate powder at a temperature of between 400° C. and 600° C.

The invention also relates to a process for preparing a composition, characterized in that it comprises the following steps:
 a. the preparation of a tumor sample,
 b. the extraction of the cytoplasmic proteins from the tumor sample,
 c. the passing of the proteins extracted in step b) through a chromatography column containing a hydroxyapatite and/or tricalcium phosphate powder as defined above,
 d. optionally at least one wash of the powder resulting from step c).

In one specific embodiment, the step of extraction of the cytoplasmic proteins aims to extract all the cytoplasmic proteins present in the tumor cells of the sample, for example previously taken from the subject to be treated. In step c) of the process for preparing the composition described above, the chromatography column may be placed under pressure manually.

The process for preparing the composition as described above may also comprise a step e) of suspending the powder resulting from step c) or d) in an injection liquid, without opening the column containing the powder.

The present invention also relates to the composition obtained according to the preparation process described above and also to said composition for therapeutic use thereof, preferably in the treatment of tumors. It may be used as a therapeutic antitumor auto-vaccine.

In addition, the present invention relates to the composition as defined above, for use thereof in the treatment of the following pathological conditions or of at least one of the following pathological conditions:
 osteosarcomas, B or T lymphomas, mammary tumors, melanomas, hemangiosarcomas, mast cell tumors, fibrosarcomas, brain or central nervous system tumors, schwannomas, mesotheliomas, seminomas, teratomas or blastomas, in a subject, and quite particularly for use thereof in the treatment of tumors in dogs, horses or cats, and for example the treatment of osteosarcomas or B or T lymphomas in dogs and also melanomas in horses or fibrosarcomas in cats.

The present invention also relates to a composition which can be obtained by means of the preparation process comprising the following steps:
 a. the preparation of a tumor sample comprising tumor cells, for example from the subject to be treated,
 b. the extraction of the cytoplasmic proteins from the tumor sample,
 c. the passing of the proteins extracted in step b) through a chromatography column containing a hydroxyapatite and/or tricalcium phosphate powder,
 d. optionally at least one wash of the powder resulting from step c),
for use thereof in the treatment of the following pathological conditions or of at least one of the following pathological conditions:
 osteosarcomas, B or T lymphomas, mammary tumors, melanomas, hemangiosarcomas, mast cell tumors, fibrosarcomas, brain or central nervous system tumors, schwannomas, mesotheliomas, seminomas, teratomas or blastomas in a subject.

The present invention also relates to compositions as described above, for therapeutic use thereof in combination with a second therapeutic agent, preferably an antitumor agent and/or a radiotherapeutic agent, for example one or more of the following compounds and/or at least one of the pharmaceutically acceptable salts thereof:
 cytotoxic drugs such as
  alkylating agents comprising nitrogen mustards (mechlorethamine, cyclophosphamide, ifosfamide, phenylalanine mustard, chlorambucil), and
  ethylenimine derivatives (triethylenethiophosphoramide), alkyl sulfonates (Busulfan), nitrosoureas (cyclohexyl chloroethyl nitrosourea, 1,3-bis(2-chloroethyl nitrosourea)), streptozotocin, triazines (dimethyltriazenoimidazolecarboxamide);

antimetabolites comprising
folic acid analogs comprising methotrexate,
pyrimidine analogs comprising 5-fluorouracil, or cytosine arabinoside,
purine analogs comprising 6-mercaptopurine, 6-thioguanine or deoxycoformycin;

natural or semi-synthetic products comprising periwinkle alkaloids (vinblastine, vincristine);

antibiotics comprising doxorubicin, mitoxantrone, daunorubicin, bleomycin, dactinomycin, mitomycin C;

enzymes such as L-aspariginase;

epipodophyllotoxins such as etoposide or teniposide;

various compounds such as cis-diaminedichloroplatinum, carboplatin, hydroxyurea and procarbazine;

antibodies targeting CD20, CD33, CD52, VEGF, HER-2neu, EGFR-1;

radioelements such as iodine 131 and calcium 45.

It also relates to the combination of therapeutic treatments comprising the administration of an effective dose of the hydroxyapatite and/or tricalcium phosphate powder according to the invention and/or of the antitumor auto-vaccines as defined above with an effective dose of a therapeutic agent, preferably an antitumor agent and/or a radiotherapeutic agent.

Furthermore, the invention is directed toward a drug combination comprising the composition as described above and at least one therapeutic agent, preferably an antitumor agent and/or a radiotherapeutic agent, for example one or more of the following compounds and/or at least one of the pharmaceutically acceptable salts thereof:

cytotoxic drugs such as
alkylating agents comprising nitrogen mustards (mechlorethamine, cyclophosphamide, ifosfamide, phenylalanine mustard, chlorambucil), and
ethylenimine derivatives (triethylenethiophosphoramide), alkyl sulfonates (Busulfan), nitrosoureas (cyclohexyl chloroethyl nitrosourea, 1,3-bis(2-chloroethyl nitrosourea)), streptozotocin, triazines (dimethyltriazenoimidazolecarboxamide);

antimetabolites comprising
folic acid analogs comprising methotrexate,
pyrimidine analogs comprising 5-fluorouracil, or cytosine arabinoside,
purine analogs comprising 6-mercaptopurine, 6-thioguanine or deoxycoformycin;

natural or semi-synthetic products comprising periwinkle alkaloids (vinblastine, vincristine);

antibiotics comprising doxorubicin, mitoxantrone, daunorubicin, bleomycin, dactinomycin, mitomycin C;

enzymes such as L-aspariginase;

epipodophyllotoxins such as etoposide or teniposide;

various compounds such as cis-diaminedichloroplatinum, carboplatin, hydroxyurea and procarbazine;

antibodies targeting CD20, CD33, CD52, VEGF, HER-2neu, EGFR-1; and radioelements such as iodine 131 and calcium 45.

Lastly, the present invention relates to a kit for carrying out the process for preparing the composition as defined above, the kit comprising the hydroxyapatite and/or tricalcium phosphate powder according to the invention, intended to interact with the extract of cytoplasmic proteins from a tumor sample, and, optionally, a device intended to receive the hydroxyapatite and/or tricalcium phosphate powder and/or a device intended to inject, in vivo, the powder having interacted with a tumor sample.

BRIEF DESCRIPTION OF SEVERAL VIEWS OF THE DRAWINGS

FIG. 1 illustrates the X-ray diffraction spectrum of a hydroxyapatite powder sintered at 600° C. according to the invention. Along the X-axis is 2 theta corresponding to the angle of diffraction and along the Y-axis is the intensity (height) of the various peaks.

FIG. 2 illustrates the measurement of the alkaline phosphatase activity after 1 h 30 min of bringing the powder into contact with cells, this being as a function of the various doses of powder.

FIG. 3 illustrates the measurement of the alkaline phosphatase activity after 3 h 30 min of bringing the powder into contact with cells, this being as a function of the various doses of powder.

FIG. 4 illustrates the measurement of the alkaline phosphatase activity after 7 h 30 min of bringing the powder into contact with cells, this being as a function of the various doses of powder.

FIG. 6 illustrates the results of the study. It involves three curves showing the survival in days and the percentage survival of dogs suffering from B lymphoma treated with the auto-vaccine according to the present invention alone (-▲-), of dogs treated with the auto-vaccine according to the present invention in combination with a chemotherapy (-♦-) and of dogs treated with a placebo in combination with a chemotherapy (-■-).

FIG. 7: protocols for chemotherapy+vaccines:
Asp corresponds to L-asparaginase at 400 IU/kg.
Vinc corresponds to vincristine at 0.75 mg/m$^2$.
Cyclo corresponds to cyclophosphamide at 250 mg/m$^2$.
Adri corresponds to adriblastine intravenously (IV) at 30 mg/m$^2$.
Lomu corresponds to lomustine at 60-80 mg/m$^2$.
Gray box corresponds to prednisone at 1 mg/kg/day.
Black box corresponds to prednisone orally at 1 mg/kg/day/2.
X corresponds to an injection of the vaccine comprising the composition according to the invention.

DETAILED DESCRIPTION OF THE INVENTION

Definitions

Figure 1:
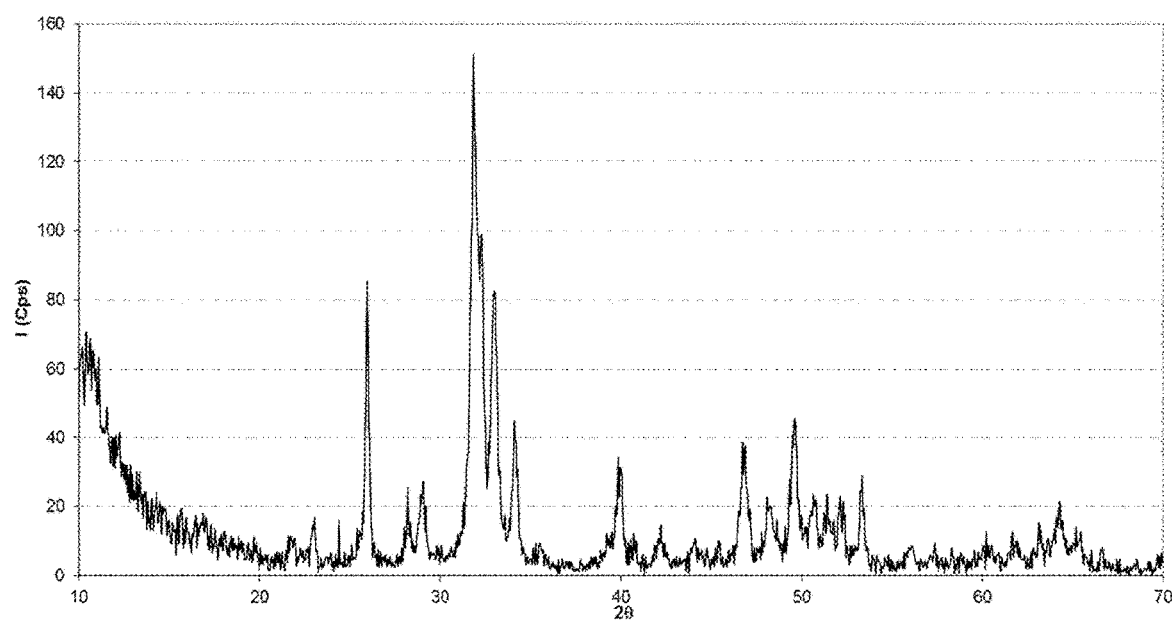
FIG. 1.

The term "hydroxyapatite" is intended to mean the mineral species of the phosphate family, of formula $Ca_5(PO_4)_3(OH)$, usually written $Ca_{10}(PO_4)_6(OH)_2$ to emphasize the fact that the mesh of the crystal structure comprises two molecules. Hydroxyapatite is the hydroxylated member of the apatite group. The OH$^-$ ion can optionally be replaced with fluorine, chlorine or carbonate.

The term "sintering" is intended to mean a process consisting in heating a powder without bringing it to melting. This process makes it possible to control the density of the powder without having any problem of variation in volume and in dimensions of the powder. It also makes it possible to obtain hard materials. The sintering can be carried out with or without binder. In the present invention, the terms "sintering" and "calcination" denote the same thing.

The term "particle size" is intended to mean the average size of the particles, and more specifically the average size of the largest dimension of non-spherical particles or diameter for spherical particles. The methods for measuring the particle size are standard, for example by laser diffraction.

The term "specific surface area" is intended to mean the actual area of the surface of an object (in this case a grain of the hydroxyapatite or tricalcium phosphate powder) as opposed to its apparent surface area. The specific surface area is of great importance for phenomena which involve surfaces, such as adsorption, absorption or heat exchanges.

The term "sample" is intended to mean whole cells taken from a tumor, ground materials, lyophilisates or else dialysates of these cells or a centrifugation pellet resulting from these cells.

The term "treatment" is intended to mean a decrease in a pathological condition and/or in its symptoms, a stagnation of the progression of the pathological condition and/or of its symptoms or a complete decline of the pathological condition and of its symptoms and/or an improvement in the quality of life. Generally, the term "treatment" involves the curative and preventive aspect.

The term "patient" or "subject" is intended to mean a human being or an animal.

The term "auto-vaccine" is intended to mean a vaccine in which the tumor antigens originate from a tumor of the patent intended to be vaccinated.

The term "antitumor agent" is intended to mean an agent capable of causing a tumor to regress, such as a hormonal agent and/or a chemotherapeutic agent.

The term "radiotherapeutic agent" is intended to mean an ionizing radiation used locally to destroy cancerous tumor cells. The ionizing radiation used is mainly X and gamma-photons (or rays), electrons, more rarely protons or neutrons. The "dose of radiation" corresponds to the amount of energy that the radiation will deposit in the tissues. It is expressed in "gray" (Gy): one gray is equal to an energy of one joule deposited in one kilogram of matter.

Process for Producing a Hydroxyapatite and/or Tricalcium Phosphate Powder

In a first aspect, the present invention relates to a process for producing a hydroxyapatite and/or tricalcium phosphate powder, characterized in that it comprises at least one step of sintering a hydroxyapatite and/or tricalcium phosphate powder at a temperature of between 400° C. and 600° C.

A large number of processes exist for producing stoichiometric calcium phosphate hydroxyapatite $Ca_{10}(PO_4)_6(OH)_2$. Preferably, the process used according to the present invention consists of a slow precipitation at high temperature, obtained by double decomposition of a calcium salt and of a phosphorus salt in a basic medium. The reaction is long, it takes place at a constant temperature in a large reaction volume and it is followed by a maturation phase and a phase of washing with water.

The precipitate thus obtained undergoes a further transformation step: solid/solution separation. The final step is carried out either by filtration, drying by stoving, and crushing, or by spray-drying using a fluidized bed. The spray-drying makes it possible to have spherical particles which, when they are used in a chromatography column, do not compact and allow the fluid to pass at a lower pressure. Moreover, these particles are easier to inject with small-diameter needles.

Whatever the solid/solution separation technique chosen, the powder will undergo two steps of transformations specific to the application of the invention: the step of particle size selection by dry screening so as to retain only the particle size band of interest, less than 25 μm or between 25 and 45 μm, then a final step during which the powder will be sintered at an optimal temperature to ensure fusion of the grains resulting in quite particular surface finishes of the powders, in particular characterized by specific surface area measurements as defined in the present invention, namely $\geq 30$ $m^2/g$. These final two steps can be reversed: selection then sintering or sintering then selection.

In one preferred embodiment, the sintering is obtained by means of a temperature increase performed starting from ambient temperature and reaching a value of approximately 600° C., for example between 500 and 800° C. The return to ambient temperature is performed, with a closed furnace, according to a free descent mode.

During the process, steps for controlling the purity of the HAP powder can be carried out by X-ray diffraction. The presence of foreign phases (predominantly lime CaO and tricalcium phosphate $Ca_3(PO_4)_2$) is sought. Thresholds of acceptance of the presence of these impurities are defined. A particular characteristic of the powder is measured; this is the width at half maximum of certain diffraction lines of the X-ray diffraction spectrum of the powder produced, in order to validate the thermal course of the sample analyzed.

Synthesis Parameters (By Way of Example):

Salts present: the chemical reaction is preferentially carried out by bringing together a solution of calcium nitrate tetrahydrate and a solution of ammonium phosphate (spontaneously formed during the mixing of aqueous ammonia with ortho-phosphoric acid) in a suitable amount to comply with the stoichiometry of the following chemical reaction.

$$10Ca(NO_3)_2, 4H_2O + 6H_3PO_4 + 20NH_4OH \rightarrow Ca_{10}(PO_4)_6(OH)_2 + 20NH_4NO_3 + 22H_2O$$

The basification of the medium is obtained by gradually adding dilute ammonia solution.

The reaction temperature is maintained at 70° C.+/−5° C. using a jacket in which a heat-transfer fluid circulates.

The reaction volume can range from 70 to 150 liters for the final mixture.

The reaction time is from 3 to 5 h 00 depending on the final volume desired.

The particle size selection is carried out by dry screening. The powder retained is less than 25 μm or between 25 and 45 μm.

The sintering is obtained by means of a slow increase in temperature in a muffle furnace. The rate of temperature increase of the furnace and also the value and the duration of the plateau will be chosen in order to obtain particular specific surface area properties of the hydroxyapatite, namely 30 $m^2/g$. Preferentially, a temperature increase is carried out starting from ambient temperature and reaching a value of approximately 600° C. (500° C.; 800° C.). The return to ambient temperature is carried out, with the furnace closed, according to a free descent mode.

Parameters of the Control

The purity of the hydroxyapatites obtained is controlled by X-ray diffraction, by comparison with the data published in an international reference: the JCPDS (Joint Committee on Powder Diffraction Standards) dossier. A percentage resemblance of the spectrum of the powder obtained to the diffraction values of a standard apatite listed in the JCPDS reference under file number 09-0432 is sought.

The expected impurities are tricalcium phosphate $Ca_3(PO_4)_2$ identified in comparison to JCPDS file 09-0169 and/or lime CaO identified in comparison to JCPDS file 04-0777. Their respective presence is tolerated in an amount of approximately 5% for each of these phases.

The measurement of the width at half maximum of the major hydroxyapatite diffraction line in terms of intensity makes it possible to have information on the thermal history of the powders produced.

On an X-ray diffraction spectrum, with an angle 2θ value of approximately 31.773 degrees+/−1%, which corresponds to the major diffraction line of hydroxyapatite, the width at half maximum is then measured. The width at half maximum to total height of the line at approximately 31.773 degrees+/−1% is then recorded in order to obtain a percentage. The more thermally treated a hydroxyapatite is, the more organized it is from a crystallographic point of view. The finer the X-ray diffraction lines of its spectrum, the smaller the width at half maximum of the main line. This measurement makes it possible to qualify the thermal history of the powder obtained. In the process according to the invention, a ratio of width at half maximum to total height of between 0.2% and 0.35% and preferably equal to 0.3%+/−10% is particularly desired.

Hydroxyapatite and/or Tricalcium Phosphate Powder

According to another of its aspects, the present invention relates to a hydroxyapatite and/or tricalcium phosphate powder obtained according to the production process as defined above.

The HAP and/or tricalcium phosphate powder according to the invention has surface properties which allow, including without coupling agent, the specific binding of active substances, and more particularly of tumor antigens, and the transport thereof to cells of the mononuclear phagocyte system.

In one more particularly preferred embodiment, the powders which exhibit at least one of the following characteristics are chosen:

a particle size G such that G≤200 μm, preferably 0<G≤25 μm or between 25 μm and 45 μm, a specific surface area SS such that SS≥30 m²/g, a percentage ratio of the width at half maximum to total height of the line on an X-ray diffraction spectrum, with an angle 2θ value of approximately 31.773+/−1%, of between 0.2% and 0.35%, preferably equal to 0.3%+/−10%.

In one even more preferred embodiment of the invention, the powders which exhibit, in addition to the particle size and/or the specific surface area as defined above, a spherical particle shape are chosen. Spherically shaped particles are particularly suitable for use according to the invention, contrary to needle-shaped particles.

The powder particle size is chosen such that the powder can penetrate into the cells to be targeted. Moreover, the amount of proteins bound to the powder varies according to the specific surface area of the powder. This parameter therefore has direct consequences on the final properties of the powder for inducing an immune response and generating a treatment of the cells or of the intended pathological condition. Finally, the spherical shape of the particles enables better binding of the specific proteins but especially better physical strength of the powder particles in the column, in particular when said column is placed under pressure manually. It is therefore important to find a correct balance between these parameters in order to have the powder and a composition for optimal therapeutic purposes.

The particle size and the specific surface area are influenced by the sintering temperature used in the process for producing the HAP and/or tricalcium phosphate powder. Indeed, when the sintering temperature is too high in the process for producing the HAP and/or tricalcium phosphate powder mentioned above, the HAP and/or tricalcium phosphate powder obtained does not have a satisfactory specific surface area since it does not make it possible to bind a sufficient amount of proteins and, when it is introduced in vivo into the patient, it will not therefore induce a sufficient immune reaction via the antigen-presenting cells. On the other hand, if the sintering temperature is too low or worthless in the process for producing the HAP and/or tricalcium phosphate powder, the powder obtained is not resistant enough and its becomes soluble at the various pHs found in the cell environment. Furthermore, once wet, the non-spherical, non-ceramized powders with an unsuitable particle size have a tendency to agglomerate. It is therefore necessary for them not to be too sensitive to wetting. Thus, with a sintering temperature that is too low, the columns made of HAP and/or tricalcium phosphate powder, on which a tumor sample will percolate for the purpose of retaining the specific proteins of the patient's tumor (and in particular the heat shock proteins), will clog and no longer allow any liquid to pass through. Furthermore, powders which are very soluble release a lot of calcium and can, in addition to the disadvantage of clogging, cause the fibrin, generally contained in the samples to be percolated, to polymerize and thus to block the column.

It is to the inventors' credit to have demonstrated that the optimal sintering temperature for preparing the HAP and/or tricalcium phosphate powder is between 400 and 600° C.

The HAP and/or tricalcium phosphate powder obtained via the production process according to the invention can then be used directly, once loaded with specific proteins of a patient's tumor, as a drug that is directly injectable into the organism for the purpose of treating said tumor.

This novel process for producing hydroxyapatite and/or tricalcium phosphate powder makes it possible to have available a novel HAP and/or tricalcium phosphate powder which is a novel more effective vector material performing simultaneously purification, vectorization in the organism and transport of active substances into target cells: antigen-presenting cells (APCs).

Process for Preparing a Pharmaceutical Composition

In another of its aspects, the present invention relates to a process for preparing a composition based on said HAP and/or tricalcium phosphate powder.

The process for preparing the pharmaceutical composition in question is characterized in that it comprises the following steps:

the preparation of a tumor sample, the extraction of the cytoplasmic proteins from the tumor sample, the passing of the proteins extracted in step b) through a chromatography column containing a hydroxyapatite and/or tricalcium phosphate powder as defined above, optionally at least one wash of the powder resulting from step c).

The preparation of the tumor sample (step a) consists in taking a cell sample in vivo, directly from the patient's tumor. Preferably, the sample is taken by puncture in the tumor, for example from a biopsy of a patient suffering from cancer. This may also involve tumor samples comprising tumor cells from the patient to be treated, already taken beforehand, said samples being ground materials, lyophilisates, dialysates or a centrifugation pellet.

The extraction of the cytoplasmic proteins from the tumor sample (step b) can be carried out according to known conventional methods. In one embodiment, the extraction method aims to extract all the cytoplasmic proteins from the tumor cells of the sample, in particular it does not comprise a step of selection or of purification of specific proteins and in particular of tumor antigens possibly contained in the cytoplasmic proteins.

Preferably, the step of extraction of the cytoplasmic proteins from the tumor sample is advantageously carried out in the following way:
- optionally freezing of the tumor tissue,
- grinding of the tumor tissue,
- solubilization or suspension of the cytoplasmic tumor antigens in an $NaHCO_3$ solution,
- centrifugation,
- separation of the pellet and of the supernatant.

The cytoplasmic protein extract is passed or percolated through a chromatography column containing the HAP and/or tricalcium phosphate powder according to the invention and as defined above (step c of the process for preparing the composition). This step consists in bringing the HAP and/or tricalcium phosphate powder according to the invention into contact with the protein extract resulting from step b of the process. The HAP and/or tricalcium phosphate powder according to the invention has the advantage of being sufficiently resistant so as not to clog in the column and thus to be able to allow the protein extract from the tumor sample which will percolate in the column to "pass through".

Advantageously, the chromatography column containing the HAP and/or tricalcium phosphate powder according to the invention is placed under pressure. The protein solution that will percolate on the column containing the HAP and/or tricalcium phosphate powder theoretically cannot pass through the powder at atmospheric pressure; for this reason, it is necessary, in this case, to use a column which can be placed under pressure manually via a piston for example. In practice, the bringing into contact can, for example, be a purification carried out using one or more columns optionally separated by a reservoir system into which or from which certain solutions can be introduced or removed and through which ground tumor material can be percolated. In one particular embodiment, if necessary, the protein(s) adsorbed onto the chromatography column can be recovered, for example, by elution from the column(s) by means of a buffer solution—preferably a phosphate buffer solution—of appropriate molarity and pH, the resulting eluate comprising tumor antigens and/or the adjuvant factors that were immobilized and sought. It is in this case a chromatography technique.

In another preferred embodiment, a composition comprising the protein(s) of a patient's tumor, adsorbed onto the HAP and/or tricalcium phosphate powder, is recovered.

The step of washing the column (step d) makes it possible to separate the HAP and/or tricalcium phosphate powder (mineral support) from the proteins of the tumor sample that have not been specifically adsorbed. This step is advantageously carried out several times with phosphate buffers or saline solution of increasing concentration. Thus, the first wash is performed with a phosphate buffer or an NaCl solution having a concentration of less than or equal to 200 mM, while a second wash can be performed with a phosphate buffer or an NaCl solution having a concentration between 300 and 500 mM.

Thus, it has been noted by the inventors that the HAP and/or tricalcium phosphate powder according to the invention, after having been brought into contact with the proteins extracted from the tumor sample, advantageously bind the specific proteins of a tumor from a given patient or the proteins which allow immune system stimulation, which represent the immunogenic proteins.

In one particular embodiment of the invention, once adsorbed, the HAP and/or tricalcium phosphate powder resulting from step c) or d) of the process for preparing the pharmaceutical composition is advantageously resuspended in an appropriate solution, preferably an injection liquid (step e) so that it can subsequently be administered to the patient. Carboxymethylcellulose (CMC), an excipient which makes it possible to facilitate injection, can advantageously be added thereto. Thus, the HAP and/or tricalcium phosphate powder carrying the specific proteins of a patient's tumor is used directly as a pharmaceutical composition or drug.

In one preferred form of the invention, the chromatography column containing the HAP and/or tricalcium phosphate powder according to the invention has the capacity to be closed at both its ends. This makes it possible to inject a suspending liquid or an injection solution or liquid into the column and to subsequently be able to directly administer to the subject or patient. The blocking of the column at both ends is advantageous since, once the injection liquid has been introduced into the column, said column is agitated in order to correctly suspend the powder according to the invention loaded with proteins, preferably with specific proteins of the patient's tumor. The non-opening of the column is a considerable advantage since it makes it possible to limit the risks of contamination.

In this particular embodiment of the invention, the process for preparing the drug comprises the succession of the following steps:
- the preparation of the tumor sample comprising tumor cells, for example of the subject to be treated,
- the extraction of the cytoplasmic proteins from the tumor sample, enabling the tumor antigens of interest to be suspended or solubilized,
- the percolation of said cytoplasmic proteins from the tumor sample through at least one chromatography column containing the HAP and/or tricalcium phosphate powder according to the invention,
- optionally a wash or washes of the chromatography column with buffer solutions of predetermined ionic strength and pH,
- d-bis) the closure of the chromatography column containing the HAP and/or tricalcium phosphate powder according to the invention,
- the suspension of the HAP and/or tricalcium phosphate powder in an injection solution.

Step d-bis) is carried out whether or not the step regarding the wash or washes of the chromatography column is carried out.

Pharmaceutical Composition

The composition according to the invention results from the production process as defined above. It corresponds to the HAP and/or tricalcium phosphate powder according to the invention loaded with the proteins adsorbed onto said HAP and/or tricalcium phosphate powder, according to the process of the invention.

Without being bound by any theory, the composition according to the invention thus obtained comprises tumor antigens non-covalently linked to the HAP and/or tricalcium phosphate powder.

In particular, in one preferred embodiment, the composition according to the invention comprises tumor antigens non-covalently linked to the HAP and/or tricalcium phosphate powder, chosen from:

proteins which bind to CD91, heat shock proteins: HSP70, gp96, HSP27 and their associated peptides, β-catenin, P-cadherin, Her-2/neu.

Preferably, at least 90%, for example at least 95%, or even at least 99% of the proteins (mol %) which bind to the cell membrane of the APCs bind to the CD91 receptors. The vaccine proteins which bind to other cell receptors were not detected by immunohistochemistry.

Figure 8:
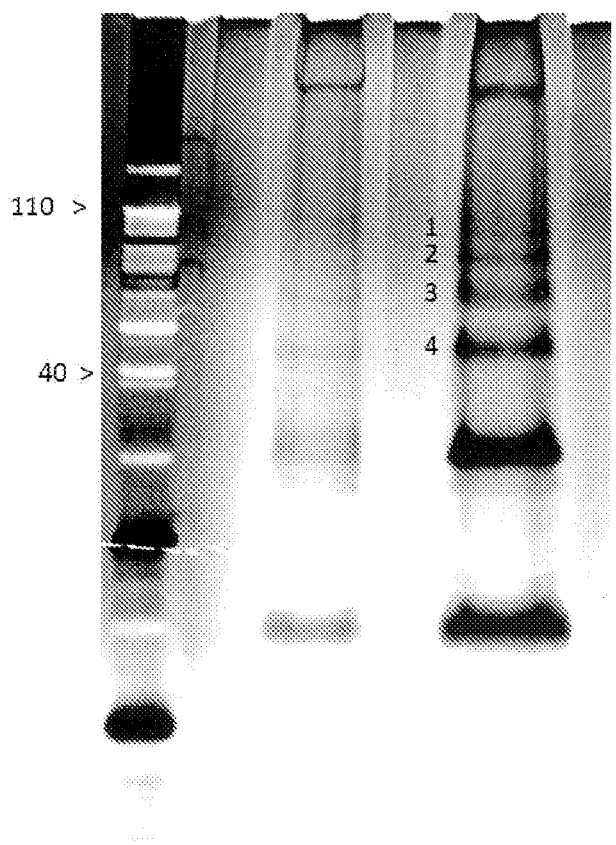
FIG. 8: Electrophoresis gel of the proteins of the compositions according to the present invention showing the presence of four migration bands between 40 and 110 kDa.

In order to characterize the composition as obtained after adsorption of tumor proteins, the inventors have noted that, after migration on an electrophoresis gel, the compositions according to the invention all comprise at least four migration bands of molecular weights between 110 and 40 kDa (see FIG. 8).

In one implementation variant, the composition according to the invention results from the preparation process comprising the following steps:

the preparation of a tumor sample comprising tumor cells, for example of the subject to be treated, the extraction of the cytoplasmic proteins from the tumor sample, the passing of the proteins extracted in step b) through a chromatography column containing a hydroxyapatite and/or tricalcium phosphate powder having a specific surface area SS such that SS≥30 m$^2$/g, optionally at least one wash of the powder resulting from step c.

The composition according to the invention may also comprise appropriate pharmaceutical excipients or carriers. In one particular embodiment, the composition according to the invention comprises carboxymethylcellulose, used as an additive to keep the powders in suspension in the solution. For example, this involves an injection solution consisting of carboxymethylcellulose at 2% in a 0.02 M NaCl solution.

Use of the Composition

The composition according to the invention as described above can be advantageously used as a drug.

It is, for example, involved in the treatment of tumors.

In one particularly preferred embodiment, the composition according to the invention is used in the treatment of pathological conditions such as osteosarcoma, B or T lymphoma, mammary tumors, melanomas, hemangiosarcomas, mast cell tumors, fibrosarcomas, brain and central nervous system tumors, schwannomas, colon cancers, leukaemias, carcinomas and adenocarcinomas, but also melanomas, mesothelioma, seminoma, teratoma and blastoma.

This composition is of use in particular in the treatment of pathological conditions in humans or in animals, for example mammals, and in particular dogs, horses or cats. It has been shown in particular that the use of the composition according to the invention gives particularly convincing and advantageous results in the treatment of canine pathological conditions, and for example in the treatment of osteosarcoma in dogs and B or T lymphomas in dogs or in the treatment of equine pathological conditions such as melanoma in horses or else in the treatment of feline pathological conditions such as fibrosarcoma in cats (cf. examples below). However, these treatments can be applied to any living being, which is human or mammalian or other animals capable of developing cancerous tumors.

The composition according to the invention therefore comprises the HAP and/or tricalcium phosphate powder having adsorbed the patient's specific tumor antigens and having been resuspended. The composition may preferably comprise the following antigens: the heat shock proteins HSP70, gp96 and HSP27 and their associated peptides, β-catenin, P-cadherin and Her-2/neu. Preferably, at least 90%, for example at least 95%, or even at least 99% of the proteins (mol %) which bind to the cell membrane of the APCs bind to the CD91 receptors. It is used for example for autologous treatments by immunotherapy, in particular as a vaccine, preferably as an antitumor vaccine. It is in particular a composition used as auto-vaccine, preferably as an antitumor auto-vaccine.

In one particular embodiment of the invention, the composition can be obtained by means of the process comprising the following steps:

the preparation of a tumor sample comprising tumor cells, for example of the subject to be treated, the extraction of the cytoplasmic proteins from the tumor sample, the passing of the proteins extracted in step b) through a chromatography column containing a hydroxyapatite and/or tricalcium phosphate powder, optionally at least one wash of the powder resulting from step c).

This composition above is then used in the treatment of the following pathological conditions or of at least one of the following pathological conditions:

osteosarcomas, B or T lymphomas, mammary tumors, melanomas, hemangiosarcomas, mast cell tumors, fibrosarcomas, brain or central nervous system tumors, schwannomas, mesotheliomas, seminomas, teratomas or blastomas in a human or animal subject.

The composition in question therefore comprises a hydroxyapatite and/or tricalcium phosphate powder having undergone a limited sintering step at a given temperature, such as between 400° C. and 600° C.

In another particular embodiment, the composition according to the invention may be used for a therapeutic use in combination with a therapeutic agent, preferably an antitumor agent and/or a radiotherapeutic agent.

As long as a state of aplasia or an aplasia-like state has not been reached in the subject to be treated, it is possible to advantageously combine the immunotherapy (associated with the powder according to the invention) and chemotherapy. The effect of chemotherapy molecules on regulatory T lymphocytes no doubt makes it possible to reequilibrate the balance of immune cells and immunization possibilities. Thus, the immunotherapy can be combined with any type of anticancer drug as long as the lymphopenia is not too great. It can be combined with anticancer drugs at cytotoxic doses or at lower doses called metronomic doses, for example at doses of cyclophosphamide of 50 mg/day combined with 2.5 mg of methotrexate on the first and second day of treatment, in the case of recurring breast cancer in humans.

The antitumor agent may be chemotherapeutic molecules. The latter are categorized as alkylating agents, antimetabolites, plant alkaloids, topoisomerase inhibitors and antitumor antibiotics. All these drugs affect mitosis and/or DNA synthesis and function to a certain degree.

They may also be agents which do not act directly on DNA, such as tyrosine kinase inhibitors and in particular the tyrosine kinase inhibitor imatinib mesylate which directly targets a molecular abnormality in certain types of cancers such as leukemia and colon cancer.

Other drugs that can be combined with the powder according to the invention modify the behavior of tumor cells without however directly attacking the cells. Hormones are in particular used for this type of adjuvant therapy.

Alkylating agents have the capacity to add an alkyl group to a large number of electronegative groups in the cell. They limit cell growth by binding the guanine molecules of the DNA double helix. The two DNA strands thus can no longer unwind or separate. The cell then can no longer divide. These agents generally do not act specifically on the cancer cell and some require a conversion in vivo into active substances (for example cyclophosphamide). As examples of alkylating agents that can be used in chemotherapy, mention may be made of: cisplatin, carboplatin (or paraplatin), ifosfamide, chlorambucil, busulfan, thiotepa. Among alkylating agents, cyclophosphamide has been shown to be particularly beneficial for immunotherapy. This molecule potentiates delayed hypersensitivity reactions. The delayed-hypersensitivity potentiation mechanism takes place through the reduction of regulatory T lymphocyte functions.

Antimetabolites act by taking the place of purines or pyrimidines, which are nucleotides that are elementary components of DNA. Base arrangements errors are thus made during DNA replication during the S phase of the cell cycle, thus stopping cell development and division and resulting in apoptosis.

Antimetabolites can be divided up into several groups according to the type of target that they reach:

antipyrimidines. Among these, mention may be made of 5-fluorouracil (5-FU) which inhibits thymidylate synthase;

antipurines. Among these, mention may be made of fludarabine which inhibits DNA polymerase, DNA primase and DNA ligase I and is exclusively active during the S phase given that these enzymes are very active during cell replication;

antifolates. Methotrexate (a folate antagonist) inhibits dihydrofolate reductase, an enzyme essential to purine and pyrimidine synthesis;

hydroxyurea.

Alkaloids are plant derivatives and block the cell division by preventing microtubule synthesis and mitotic spindle formation, vital for cell division.

Among the alkaloids that can be used in the present composition, mention may be made of:

vinca alkaloids such as vincristine, vinblastine or vinorelbine which bind to specific sites on tubulin and inhibit the assembly of tubulins into microtubules, essential to cell division, taxanes such as paclitaxel (from *Taxus brevifolia*), with its synthetic derivative docetaxel), which inhibits cell division by stimulating tubulin polymerization, improving the formation and stability of microtubules which cannot then degrade, thus preventing chromosomes for migrating to the poles of the nucleus, epothilones, produced from a myxobacterium, which have the same mechanism as taxanes and appear to have a similar anticancer activity.

Topoisomerase inhibitors act by definition on topoisomerases which are essential enzymes that maintain the topology of DNA. The inhibition of topoisomerase type I or type II impairs both DNA transcription and DNA replication by disturbing DNA supercoiling.

As topoisomerase type I inhibitors, mention may be made of camptothecin.

As topoisomerase type II inhibitors, mention may be made of amsacrine, anthracyclines and epipodophyllotoxin derivatives.

There are numerous antitumor antibiotics of different types. Generally, they prevent cell division by several means:

DNA binding, by inserting between two adjacent nucleotide bases and preventing them from separating, RNA inhibition, preventing the synthesis of enzymes, impairing cell replication.

They are produced by various strains of the bacterium *Streptomyces*.

Among these, mention may be made of anthracyclines: doxorubicins and daunorubicin which also inhibit topoisomerase type II, actinomycin D, mitomycin C, plicamycin, bleomycin which acts only by oxidizing the DNA-bleomycin-Fe(II) complex, thus forming free radicals which bring about chromosomal damage and aberrations. Among them may be categorized the antiasparagines (L-asparaginase). Asparagine is an amino acid that is essential for certain cancer cells and that they are incapable of synthesizing, unlike normal cells. They therefore depend on circulating asparagine.

A new class of anticancer drugs also exists, the combination of which with antitumor vaccines is of interest: monoclonal antibodies such as anti-VEGF, anti-CD20, anti-CD19 and anti-CD30 antibodies, and the like.

The biological consequences of ionizing radiation on living tissues was discovered shortly after the discovery of X-rays. Most of the radiobiological data show that DNA is the most significant target for the biological effects in the form of base bonding, and strand breaking at the level of the sugar-phosphate bond. In the cell, the radiolesion induced causes mutations, and/or an impossibility for cell division to occur. These consequences are more significant for proliferating cells such as tumor cells, but are also significant for healthy cells, leading to equally significant side effects.

Four major radiotherapy techniques can be distinguished: external radiotherapy, radiosurgery, brachytherapy and metabolic radiotherapy. Each of them has its indications depending on the type of tumor and its location.

In external radiotherapy, the most widely used, the radiation source is outside the subject to be treated. Cobalt bombs, which use a cobalt 60 γ-radioactive source, have practically disappeared to the benefit of linear electron accelerators producing high-energy X-ray beams and electron beams. There are three main techniques: conventional radiotherapy, 3D (three-dimensional) conformational radiotherapy and helical tomotherapy or radiotherapy.

In brachytherapy, the radioactive source is placed, for a limited period (usually a few hours) or definitively, inside the subject to be treated, in the tumor or in a cavity in contact therewith. Three main techniques, themselves subdivided into subtechniques according to their dose flow rate (low flow rate and high flow rate) and their type of loading (manual or staggered). They are interstitial brachytherapy, intracavitary brachytherapy and intraluminal brachytherapy.

In metabolic radiotherapy, the non-sealed radioactive source, in liquid or gel form, is injectable and will bind to the target cells.

Depending on the type of the tumor, on its location, on its size, on its spread and on its stage, on the general condition of the subject to be treated and on the associated symptoms, three very different situations are distinguished, in which radiotherapy will be used for very precise purposes:

Curative radiotherapy, the objective of which is to irradiate most of the cancer cells in order to bring about control or even curing of the cancer. This entails an absence of remote lesions. It is indicated in approximately half the irradiations. It is advantageously used alone or in combination with surgery and/or chemotherapy. The dose required depends on the type and the volume of the tumor, some being very radiosensitive while others are radioresistant. The usual protocol delivers a dose of 10 Gy per week at a rate of five sessions of 2 Gy per day. The total dose varies, as appropriate, from 30 to 70 Gy.

Palliative radiotherapy, the objective of which is not in this case to cure the cancer, but to relieve the subject to be treated with light doses, making it possible to reduce the pain resulting from cancer that is too advanced that is to be treated. It addresses cancers that have progressed too far locally or are metastatic. Since the treatment is palliative, it should be of short duration and not very aggressive, so as to cause the patient as little inconvenience as possible.

Symptomatic radiotherapy, the objective of which is to relieve a major symptom that is particularly troublesome for the patient. Its effectiveness is: analgesic, hemostatic or decompressive.

In all these techniques, the radiation used is X- and gamma-photons (or rays), electrons, or more rarely protons or neutrons.

The invention therefore also relates to a therapeutic treatment combination comprising the administration of an effective dose of the hydroxyapatite and/or tricalcium phosphate powder as defined above and/or of the composition of the invention as defined above with at least one effective dose of a therapeutic agent, preferably an antitumor agent and/or a radiotherapeutic agent as defined above.

The administration of the composition according to the invention (for example antitumor auto-vaccine) and of the antitumor agent can be carried out concomitantly, in the form of a single composition or of two separate compositions, or at different times, according to the optimal protocol according to the patient and the pathological condition to be treated.

The inventors have shown, notably, a complete remission of certain tumors, in particular in dogs, when the composition according to the invention is used in combination with another antitumor agent (cf. examples below).

The composition as defined above combined with at least one therapeutic agent such as an antitumor agent defined above and/or at least one radiotherapeutic agent therefore also represents a drug combination covered by the present invention.

The composition according to the invention is preferably administered by injection.

When it is a question of the drug combination, the injection of the composition and of the therapeutic agent may be simultaneous or independent over time.

One of the advantages of the composition according to the invention is that it is particularly reliable in terms of contamination. This is because the process for producing same can be carried out virtually in a totally closed environment and with the same HAP and/or tricalcium phosphate powder, thereby limiting the risks of contamination. There is preferably no transfer from one HAP and/or tricalcium phosphate support to another and it is the HAP and/or tricalcium phosphate powder having been used for the purification and the binding of the biological materials (preferably the specific proteins of the patient's given tumor and more particularly the heat shock proteins) that will be injected directly without being sampled beforehand. The pharmaceutical composition is thus made up of both the HAP and/or tricalcium phosphate powder and also the biological materials which are adsorbed onto said powder.

Another advantageous characteristic of the composition stems from the fact that it is intended to be phagocytized by macrophages and/or other APCs and/or dendritic cells. It also allows the in vivo transport of one or more active substances. In other words, the HAP and/or tricalcium phosphate powder according to the invention makes it possible to vectorize any substance/molecule that can be adsorbed onto said powder, using the antigen-presenting cells (APCs) or other analogous cells.

The invention is therefore also directed toward a composition characterized in that it is intended to activate macrophages and/or other APCs, i.e. to bring about the synthesis of substances chosen from the group comprising cytokines, lymphokines and growth factors, and/or render dendritic cells mature.

Once injected into a connective tissue, the composition according to the invention can bring about a local afflux of macrophages, dendritic cells and/or other APCs presenting the antigen(s) adsorbed onto the HAP and/or tricalcium phosphate powder.

According to one advantageous mode, the composition according to the invention, once administered in vivo or in vitro, allows sustained release (for example for a few hours to several days) of the active substance(s) adsorbed onto the HAP and/or tricalcium phosphate powder.

When it is used in the form of a galenical unit, the pharmaceutical composition or drug according to the invention is advantageously used in an amount of between 15 and 100 μg dose/galenical unit.

In one particular embodiment, one dose administered by injection to the patient comprises between 30 and 50 mg of hydroxyapatite and between 1000 and 2000 μg of proteins; preferably 100%, or at least 90%, for example at least 95%, or even at least 99% of the proteins (mol %) which bind to the cell membrane of the APCs bind to the CD91 receptors. For the purposes of the invention, the term "CD91" refers to the transmembrane receptor expressed in humans, in particular of galenic (Uniprot) protein sequence Q07954, also called LRP1, and which interacts with HSP proteins, in particular gp96.

In one particular form of use of the composition, it is advantageous to carry out a revaccination of the subjects affected. Thus, in one specific embodiment, it is preferable to perform two successive steps of administration of the antitumor auto-vaccine. In particular, the second vaccine is preferably obtained from a new tumor sample taken from the subject affected.

Indeed, it is assumed that the anti-tumor treatments eliminate the various constitutive clones of a tumor differentially owing to their variable sensitivity to treatments. The most sensitive clones would be eliminated and the most resistant would develop so as to occupy the niche left by the previous ones. For this reason, when the tumor escapes the first vaccine response, it is justified to proceed with a second vaccine from a new sample in order to stimulate the immune system against all the abnormal proteins characterizing the new dominant clones.

Kit for Carrying Out the Process for Preparing the Composition

The invention is also directed toward a kit for carrying out the process for preparing the composition as defined above (with or without step of sintering the powder), characterized in that it comprises the hydroxyapatite and/or tricalcium phosphate powder as defined above, intended to interact with the cytoplasmic proteins extracted from a tumor sample.

This kit optionally comprises a device intended to receive the hydroxyapatite and/or tricalcium phosphate powder and/or a device intended to administer, preferably to inject, in vivo, said powder having interacted with the cytoplasmic proteins from a tumor sample. The device intended to administer the powder in vivo may be, for example, a syringe.

This kit advantageously allows a practitioner in human or animal medicine to purify the tumor-specific peptides by virtue of HAP and/or tricalcium phosphate powders, and to bind them to these same powders which will subsequently be injected into a patient. Preferably, the tumor-specific peptides bound to the heat shock proteins bound to the HAP and/or tricalcium phosphate powder originate from the patient into whom the powder will be readministered, preferably reinjected. The injection into the patient is preferably carried out in the tissues subcutaneously or intradermally.

In one implementation variant of the kit, the latter optionally comprises one or more of the following means, in addition to the hydroxyapatite and/or tricalcium phosphate powder:

the means for taking the tumor sample, the means for extracting the cytoplasmic proteins from the tumor sample, such as an $NaHCO_3$ or $Na_2CO_3$ solution, the means for binding the tumor-specific proteins to the hydroxyapatite and/or tricalcium phosphate powder, the means for suspending the HAP and/or tricalcium phosphate powder loaded with tumor-specific proteins, the means for administering, preferably injecting, said suspension in vivo.

It emerges in particular from the above disclosure of the invention that the HAP and/or tricalcium phosphate particles according to the invention are a good vector for transporting the specific proteins of a patient's tumor into macrophages and antigen-presenting cells and that they are suitable for treating pathological conditions such as cancer. This will be seen more clearly on reading the following examples.

EXAMPLES

Example 1

Process for Preparing the HAP Powder

The process for preparing the stoichiometric calcium phosphate hydroxyapatite $Ca_{10}(PO_4)_6(OH)_2$ consists of a slow precipitation at high temperature, obtained by double decomposition of a calcium salt and of a phosphorus salt in a basic medium. The reaction is long, it takes place at constant temperature in a large reaction volume and it is followed by a maturation phase and a phase of washing with water.

The precipitate thus obtained undergoes a further transformation step: solid/solution separation. The latter step is carried out either by filtration, drying by stoving and crushing, or spray-drying using a fluidized bed.

Whatever the solid/solution separation technique chosen, the powder will undergo two steps of transformations specific to the application of the invention: The particle size selection step by dry screening so as to retain only the particle size band of interest, of less than 25 µm or of between 25 and 45 µm, then a step during which the powder will be sintered at an optimal temperature so as to ensure fusion of the grains resulting in quite particular surface finishes of the powders, in particular characterized by specific surface area measurements as defined in the present invention, namely ≥30 m²/g.

During the process, steps for controlling the purity of the HAP powder are carried out by X-ray diffraction. The width at half maximum of certain diffraction lines of the X-ray diffraction spectrum of the powder produced is measured, in order to validate the thermal course of the sample analyzed.

Synthesis Parameters:

Salts present: the chemical reaction is preferentially carried out by bringing together a solution of calcium nitrate tetrahydrate and a solution of ammonium phosphate (spontaneously formed during the mixing of aqueous ammonia with ortho-phosphoric acid) in a suitable amount to comply with the stoichiometry of the following chemical reaction.

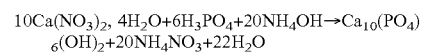

$10Ca(NO_3)_2, 4H_2O+6H_3PO_4+20NH_4OH \rightarrow Ca_{10}(PO_4)_6(OH)_2+20NH_4NO_3+22H_2O$ The basification of the medium is obtained by gradually adding dilute ammonia solution The reaction temperature is maintained at 70° C.+/−5° C. using a jacket in which a heat-transfer fluid circulates.

The reaction volume can range from 70 to 150 liters for the final mixture.

The reaction time is from 3 to 5 h 00 depending on the final volume desired.

The particle size selection is carried out by dry screening. The powder retained is preferentially less than 25 µm or between 25 and 45 µm.

The sintering is obtained by means of a slow increase in temperature in a muffle furnace. The rate of temperature increase of the furnace and also the value and the duration of the plateau will be chosen in order to obtain particular specific surface area properties of the hydroxyapatite, namely ≥30 m²/g. Preferably, a temperature increase is carried out so as to reach a value of 600° C. (−100° C.; +200° C.). The heating is stopped and a slow free descent is initiated until a return to ambient temperature is obtained, with the furnace closed.

Parameters of the Control

The purity of the hydroxyapatite powder obtained is controlled by X-ray diffraction, by comparison with the data published in an international reference: the JCPDS (Joint Committee on Powder Diffraction Standards) dossier. A percentage resemblance of the spectrum of the powder obtained to the diffraction values of a standard apatite listed in the JCPDS reference under file number 09-0432 is sought.

The expected impurities are tricalcium phosphate $Ca_3(PO_4)_2$ and/or lime CaO. Their presence is tolerated in an amount of approximately 5% for each of these phases.

The measurement of the width at half maximum of the major hydroxyapatite diffraction line in terms of intensity makes it possible to have information on the thermal history of the powders produced.

On an X-ray diffraction spectrum, with an angle 2θ value of approximately 31.773 degrees+/−1%, which corresponds to the major diffraction line of hydroxyapatite, the width at half maximum is then measured. The width at half maximum to total height of the line at approximately 31.773 degrees+/−1% is then recorded in order to obtain a percentage. The more thermally treated a hydroxyapatite is, the more organized it is from a crystallographic point of view. The finer the X-ray diffraction lines of its spectrum, the smaller the width at half maximum of the main line. This measurement makes it possible to qualify the thermal history of the powder obtained. In the process according to the invention, a ratio of width at half maximum to total height equals 0.301%.

FIG. 1 illustrates the X-ray diffraction spectrum of a hydroxyapatite powder sintered at 600° C. according to the invention. Along the X-axis is 2 theta corresponding to the angle of diffraction and along the Y-axis is the intensity (height) of the various peaks.

|      | 100%  | half maximum | 2 theta bottom limit | 2 theta top limit | width at half maximum | width at half maximum/ height |
|------|-------|--------------|----------------------|-------------------|----------------------|-------------------------------|
| 0    | 31.85 | 142.7        | 71.3                 | 31.67             | 32.265               | 0.595                         | 0.417% |
| 300  | 31.88 | 134.7        | 73.3                 | 31.645            | 32.135               | 0.490                         | 0.364% |
| 600  | 31.85 | 152.3        | 76.1                 | 31.677            | 32.135               | 0.458                         | 0.301% |
| 900  | 31.85 | 270          | 135                  | 31.742            | 31.946               | 0.204                         | 0.076% |
| 1000 | 31.81 | 332          | 166                  | 31.731            | 31.903               | 0.172                         | 0.052% |

At the end of this process, the following characteristics are observed on the powder:
1) the particles have a particle size of less than 200 μm and the majority is between 0 and 25 μm or between 25 and 45 μm;
2) the particles have a specific surface area of greater than 30 m$^2$/g;
3) the particles are spherical or irregular in shape depending on the production options chosen;
4) on the X-ray diffraction spectrum under the control conditions defined above, the ratio of width at half maximum to total height is equal to 0.301%.

Example 2

Process for Preparing the Composition a) Preparation of the Tumor Sample

A fraction of approximately 1 cm$^3$ of a tumor sampled beforehand during a surgical biopsy or a diagnostic biopsy using a trephine is taken sterilely and then cut up into small fragments. They are placed in a sterile grinding tube prefilled with 1 g of alumina beads 1 mm in diameter. 4 ml of a 0.03 M Na$_2$CO$_3$ solution are added thereto (1V/1V). The tube is then placed in a grinder for 3 minutes. The operation is repeated until a liquid ground material is obtained. The grinding solution is transferred into a centrifugation tube using a sterile pipette.

b) Extraction of the Cytoplasmic Proteins from the Tumor Sample

A ground biopsy is centrifuged at 6000 rpm for 5 minutes in order to remove the membrane debris. The supernatant is kept, transferred into a sterile centrifugation tube and diluted to 50% (1V/1V) in a supersaturated solution of ammonium sulfate (NH$_4$)$_2$SO$_4$, then placed at 4° C. for 1 h and then finally, centrifuged at 6000 rpm for 30 minutes. The pellet resuspended in 1 ml of a 0.02 M solution of (Na$_2$HPO$_4$; NaH$_2$PO$_4$) at pH 6.8 is then diluted to 75% (1V/2.3V) in the same ammonium sulfate solution.

c) Passing of the Proteins of Step b) through a Chromatography Column Containing the HAP Powder The powder prepared by means of the process of example 1 is placed in a chromatography column, the bottom end of which is stoppered. The content of the tube, obtained at the end of step b), is poured into the chromatography column and passed through the hydroxyapatite (calcium phosphate) powder. The top end of the column is stoppered and the column is then vigorously agitated and then left to stand for 3 minutes. A syringe filled with air is fitted to the top end of the column, the bottom end of which is unstoppered. A slow pressure is exerted on the syringe piston in order to cause all the liquid to pass through the HAP column thus brought into contact with the proteins from the tumor sample.

d) Washing of the Powder Resulting from Step c) or Composition

The column is then washed with a solution of phosphate buffer or of NaCl at 0.02 M and pH 6.8.

e) Suspension of the Composition

The phosphate buffer is then removed by pressure with the syringe and then replaced with the injection solution. After having blocked the bottom end of the column resulting from step d), 4 ml of an injection solution consisting of carboxymethylcellulose at 2% in a 0.02 M NaCl solution are introduced into the HAP column.

The HAP column loaded with the tumor (biopsy)-specific proteins is blocked at the two ends and then agitated in order to suspend the HAP powder in the injection liquid.

Once the powder is in suspension, the composition is ready to use. It will be sufficient to connect 1 ml syringes in order to pump 0.5 ml directly into the column and to inject this dose into the patient to be treated.

Example 3

Kit Comprising HAP Powder According to the Invention and Use Thereof

The kit according to the invention should allow a practitioner in animal or human medicine to purify the specific peptides of a patient's tumor, this being by means of bringing the HAP powders according to the invention into contact with the tumor sample. This HAP powder will bind these tumor-specific peptides so as to subsequently be injected into the tissue subcutaneously or intradermally.

Content of the Kit:

| concentration | containing | Content in ml | chemical composition | designation |
|---------------|------------|---------------|----------------------|-------------|
| 0.03M | 5 ml | 4 | Na$_2$CO$_3$ or NaH CO$_3$ | I |
| saturation | 10 ml | 8 | (NH$_4$)$_2$ SO$_4$ | II |
| 0.02M pH 6.8 | 10 ml | 8 | Na$_2$HPO$_4$; NaH$_2$PO$_4$ | III |
| 2% CMC in 0.02M NaCl | 5 ml | 4 | CMC + NaCl | IV |

Use of the Kit (Procedure):

The steps of example 2 above are carried out.

This kit contains the material strictly necessary in order to extract the cytoplasmic proteins from a tumor sample, to purify the cellular HSPs and to bind them to the HAP powders and to prepare the suspension to be injected. It combines in an original manner the saline solutions in order to extract the cytoplasmic proteins and a closed device which makes it possible to, sterilely and under pressure, pass a solution of proteins through a closed column containing a biocompatible and injectable powder according to the invention, to wash the powder in order to remove the proteins of no biological interest, to disperse the powders in an injection solution and to load syringes without opening the column. The non-opening of the column is a considerable advantage since it makes it possible to limit the risks of contamination.

The kit also contains sterile 1 ml syringes and sterile needles, small-format and large-format labels, and sterile tubes for centrifuging and taking samples.

Example 4

Effect of the Powder According to the Invention on Stimulation of the Inflammasome The inflammasome is an oligomeric protein complex involved in inate or non-specific immunity. It is formed following the recognition of various inflammatory signals (LPS, uric acid crystals, various viral and bacterial components) by proteins of the NLPR family. The inflammasome promotes maturation of the inflammatory cytokines IL-1β and IL-18, by cleaving them via the activation of its caspase 1. The inflammasome is responsible for the activation of inflammatory processes, and can induce a phenomenon of pyroptosis, a program of cell death other than apoptosis. Although the inflammatory cytokines synthesized in the tumor can be involved in the development of the tumor, the activation of the inflammasome by adjuvants remote from the tumor is essential to the cross priming of T lymphocytes and to the recruitment of APCs.

Several HAP powders were tested with regard to their capacity to stimulate the inflammasome. The powders are used as a second signal (after a ligand (PMA) that is active on TLR receptors) and are brought into contact with cells (THP1 from Invivogen®) which will produce IL1b. The bringing into contact is carried out for 1 h 30 min, 3 h 30 min and 7 h 30 min. This IL1b will act on a second cell line which has an alkaline phosphatase gene coupled to the transcription factor (NF-κB) on which IL-1b acts. After reaction with its substrate, the alkaline phosphatase is assayed by optical density (OD). The activation of the alkaline phosphatase is in this case a reflection of the activation of the immune system carried out in the antitumor process. There is therefore a correlation between the measurement of the alkaline phosphatase activity and the activation of the inflammasome (NLPR3).

The measurement of the amount of alkaline phosphatase is carried out by spectrophotometry according to conventional methods.

The powders with the following characteristics were tested.

| Powder | Amount of HAP (as %) | Shape of the powder particles | Particle size (in μm) | Sintering temperature for preparing the powder (in ° C.) | Specific surface area (in m²/g) |
|---|---|---|---|---|---|
| A | >98 | irregular | 0-25 | 900 | 2.9 |
| B | >98 | irregular | 0-25 | 500 | 33.53 |
| C | >98 | spherical | 80-125 | 1180 | 0.6 |
| D | >98 | irregular | 80-160 | 1180 | 0.77 |
| E | >98 | spherical | 22-45 | 1180 | 0.9 |
| F | >98 | spherical | 0-25 | 600 | 31.11 |
| G | >98 | irregular | 0-25 | 600 | 34.69 |
| H | >98 | acicular | 0-25 | 0 | 10.11 |

Figure 2:
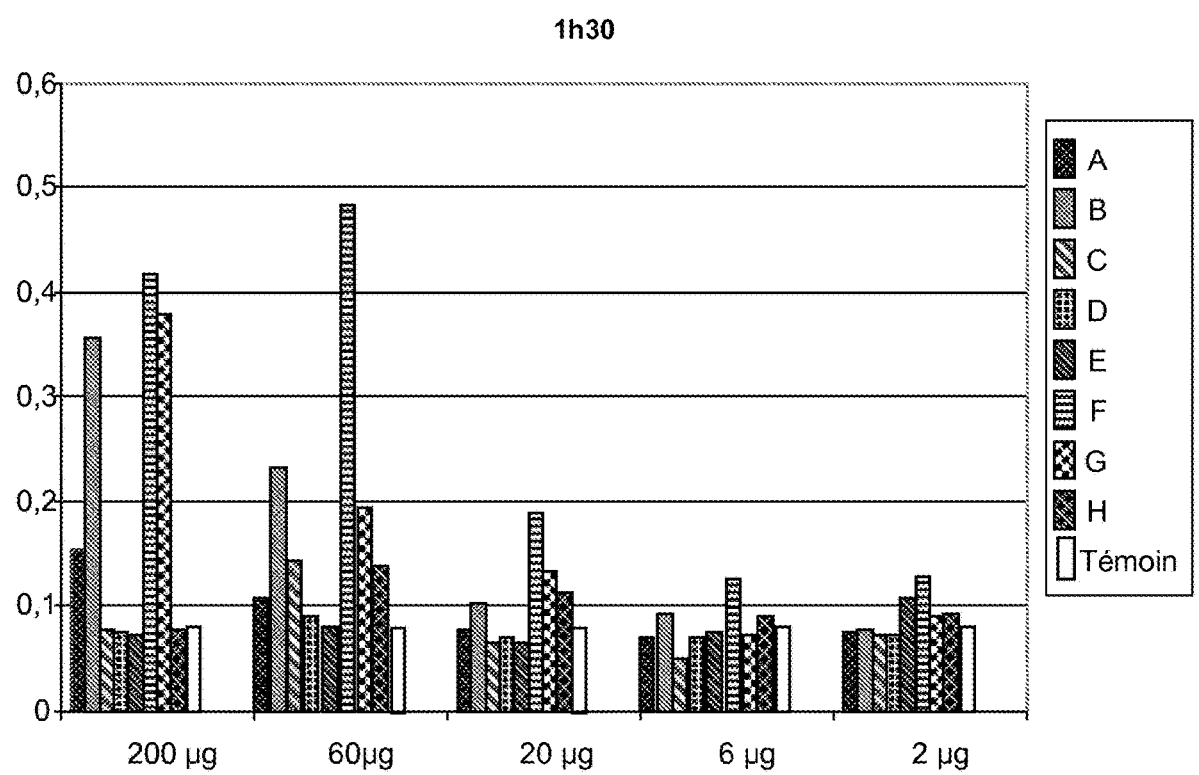
FIG. 2.

FIG. 2 illustrates the measurement of the alkaline phosphatase activity after 1 h 30 min of bringing the powder into contact with cells, this being as a function of the various doses of powder.

Figure 3:
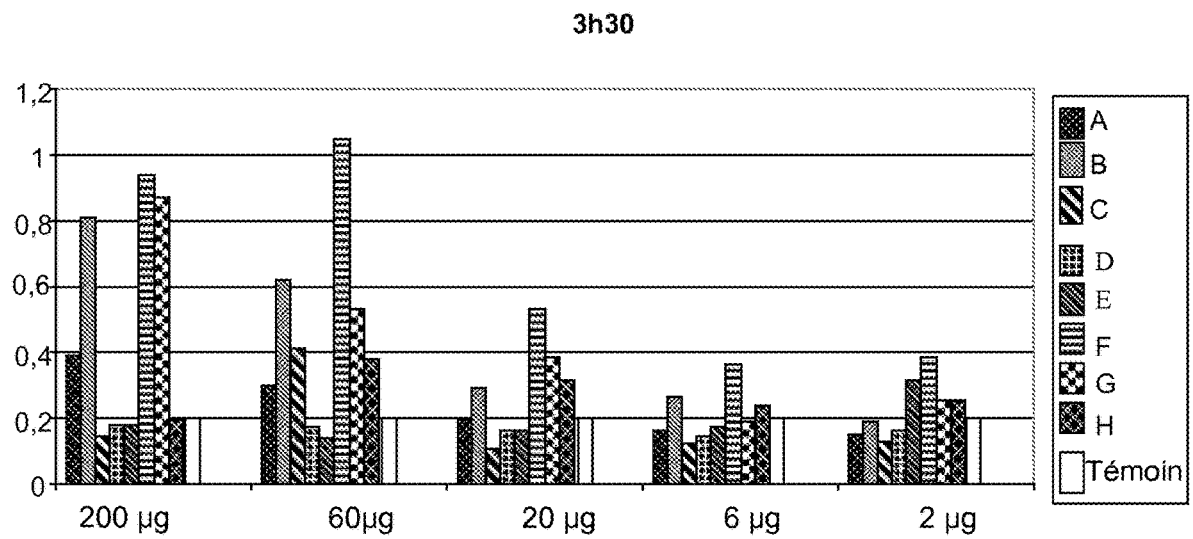
FIG. 3.

FIG. 3 illustrates the measurement of the alkaline phosphatase activity after 3 h 30 min of bringing the powder into contact with cells, this being as a function of the various doses of powder.

Figure 4:
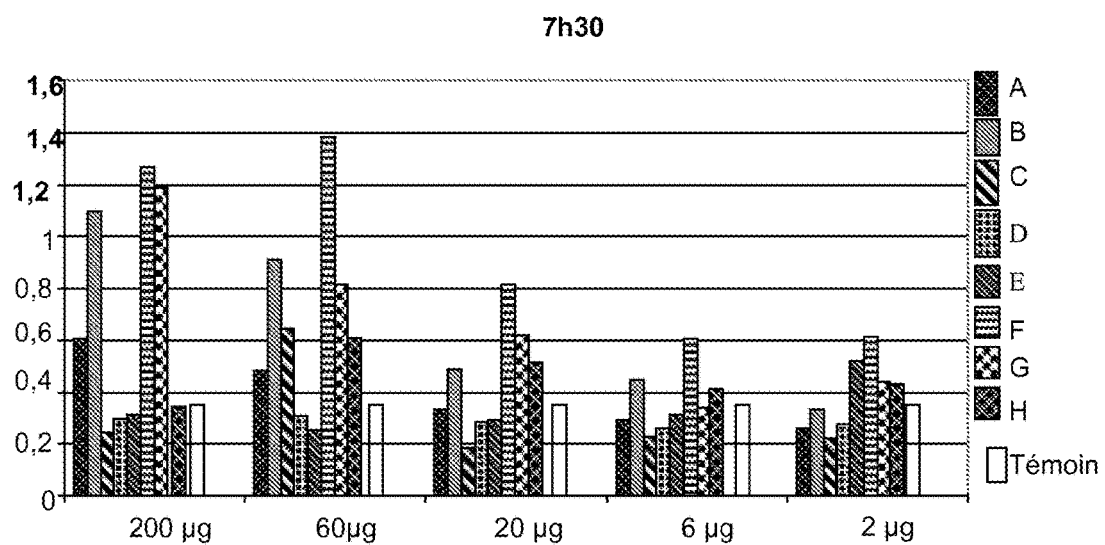
FIG. 4.

FIG. 4 illustrates the measurement of the alkaline phosphatase activity after 7 h 30 min of bringing the powder into contact with cells, this being as a function of the various doses of powder.

According to the results, it appears that the powders B, F and G allow a better activation of the inflammasome, in particular with doses of between 20 μl and 200 μl. These powders can therefore intervene in the activation of the cytotoxic immune system via the antitumor mechanism. The powders B, F and G exhibit all three of the common characteristics, namely a particle size of between 0 and 25 μm, a specific surface area of greater than 30 m²/g and the sintering being carried out at a temperature of 500° C. and 600° C.

Example 5

Effect of the Proteins Desorbed from the Vaccine Particles Prepared According to the Invention and Brought into Contact on RAW 264.7 Cells (ATCC)

The proteins originating from a vaccine prepared as described from a dog osteosarcoma are desorbed from the particles using a $K_2HPO_4$ solution. These proteins are labeled with a biotin molecule using sulfo-NHS-biotin. They are then brought into contact with RAW cells in culture optionally after the CD91 molecules have been optionally blocked by anti-CD91 antibodies. The cells are then brought into contact with a peroxydase-labeled streptavidin and revealed with a diaminobenzidine. The positive control is a gp96 labeled and used in the same way.

It appears that all the cells are labeled with the proteins purified from the vaccine and also with the gp96 molecules. In the two cases, the labeling is inhibited by bringing the cells into contact with an anti-CD91 beforehand. This demonstrates that the proteins derived from the vaccine bind to the antigen-presenting cells only via CD91 receptors, this would therefore correspond to heat shock proteins (HSPs).

Example 6

Effect of the Composition According to the Invention in the Treatment of Osteosarcoma in Dogs Osteosarcoma is a malignant primary bone tumor. It is preferably located on the long bones. Dogs suffering from osteosarcoma have a very unfavorable vital prognostic. The average survival is approximately two months. Amputation and chemotherapy give better results but they are not always possible.

In the knowledge that heat shock proteins can become linked to peptides synthesized by cancer cells and activate the immune system (via T lymphocytes and in particular CD8 cells), a method of vaccination based on the injection of powders according to the invention carrying proteins specific to the dog's tumor (these are mainly heat shock proteins linked to tumor peptides) was tested in healthy dogs and dogs suffering from osteosarcoma. It was measured whether the vaccination with these powders could have a clinical effect on these healthy and pathological dogs.

According to the process described in example 2, tumor proteins originating from biopsies from dogs suffering from osteosarcoma were adsorbed onto an HAP powder according to the invention. Eight injections were given to dogs at various time intervals. After this auto-vaccine, the overall survival and the survival without progressions of the osteosarcoma were measured in each dog and compared to the data in the literature.

No local or systemic side effect was demonstrated in the dogs after injection. It is noted that the overall survival rate in all dogs having received an injection (healthy or suffering from an osteosarcoma) is better than the average survival rate of dogs which is reported in the literature.

It is also demonstrated that the survival without progression of the disease is very close to the overall survival and that the inflammation zone of the tumor zone regresses after each injection.

Remodeling of the region of the tumor after vaccination is observed with X-rays.

These results show that the auto-vaccines with the HAP powder according to the invention loaded with heat shock proteins from a tumor from the dog (composition according to the invention) represent a good adjuvant therapy for eliminating the cells disseminated during the progression of a tumor or cancer and/or slowing down the development of metastases.

Example 7

Effect of the Composition According to the Invention Compared with Chemotherapy in the Treatment of Osteosarcoma in Dogs 22 dogs with osteosarcomas were divided up into three different groups corresponding to three different treatments:
 a first group of dogs (5 dogs) receives no treatment,
 a second group of dogs (10 dogs) receives the treatment by chemotherapy alone as published in the literature (Takuo Shida et al. Low-dose chemotherapy for canine appendicular osteosarcoma, Journal of Japan Veterinary Cancer Society, Vol. 2, No. 1, 1-6 2011),
 a third group of dogs (7 dogs) is vaccinated with the composition according to the invention as obtained at the end of example 2 (hydroxyapatite powder carrying cytoplasmic proteins from the tumor of the dog to be treated).

The overall survival, in days, of all the dogs in this study was observed.

Figure 5:
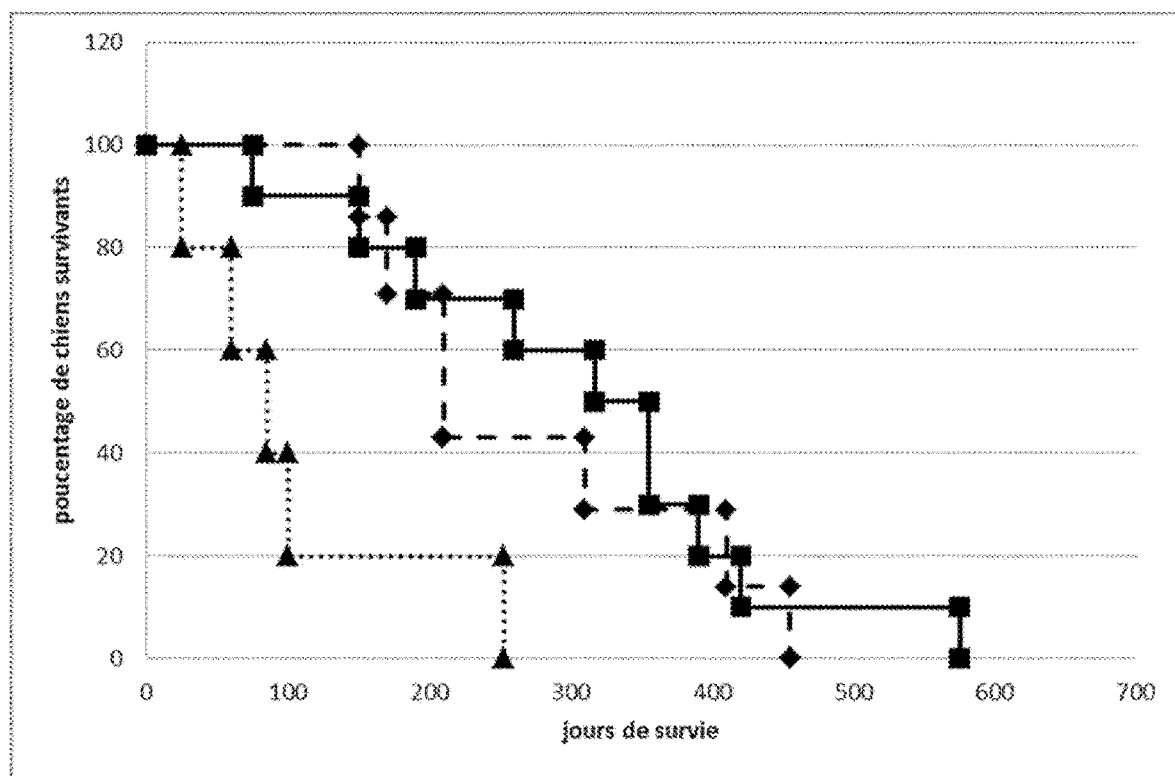
FIG. 5: ▲: no treatment; ■: vaccine according to the invention; ♦: chemotherapy according to Takuo Shida et al. Low-dose chemotherapy for canine appendicular osteosarcoma, Journal of Japan Veterinary Cancer Society, vol. 2, No. 1, 1-6 2011.

FIG. 5 illustrates these results of survival of the non-treated dogs/dogs receiving chemotherapy/dogs vaccinated with the composition according to the invention.

The dogs having received no treatment have a survival of approximately 250 days, while the dogs treated by chemotherapy have a survival of approximately 580 days and the dogs treated by immunotherapy have an overall survival of approximately 450 days. This shows that the immunotherapy using the composition according to the invention gives very satisfactory results which are comparable to the results obtained with chemotherapy, while having fewer drawbacks than chemotherapy, which is very restricting and has many side effects. No side effect was noted in the dogs treated by immunotherapy with the composition according to the invention.

Example 8

Effect of the Composition According to the Invention in the Treatment of B Lymphomas in Dogs Lymphoma is a cancer of the lymphatic system which develops to the cost of lymphocytes. It is characterized by malignant cell proliferations in the secondary lymphoid organs. Among the aggressive malignant lymphomas are lymphomas of phenotype B and of phenotype T, also called B and T lymphomas.

A study of the effect of the composition according to the invention on lymphomas was carried out on 50 dogs suffering from histologically established B lymphomas.

The dogs were typed according to WHO standards:
 Stage I: involvement of one lymph node or one organ;
 Stage II: regional involvement of several lymph nodes with or without the tonsils;
 Stage III: polyadenomegaly;
 Stage IV: liver and/or spleen involvement in addition to stages I to III;
 Stage V: bone marrow and blood involvement in addition to stages I to IV.

The substages (a) corresponding to without clinical signs and (b) with clinical signs are also evaluated.

A lymph node is removed from a dog with a B lymphoma and the immunotherapy doses are prepared according to the protocol mentioned above with the process for preparing the composition and the vaccination kit (cf. examples 1 to 4).

One dose is injected subcutaneously once a week for 4 weeks and then once a month for 4 months. 8 doses are therefore used.

Two groups of dogs were formed:
 a. the first group received these immunotherapy doses combined with a chemotherapy protocol including asparaginase, vincristine, adriblastine, cyclophosphamide, lomustine and prednisone;
 b. the second group received only the immunotherapy doses.

These various data were then compared with the data from the literature.

Dogs (n=16) at a very advanced stage (Va or Vb) are exposed since their life expectancy is very short. The data from the literature and the experimental data gives the following results:

|  | Median survival (in days) | Average survival (in days) |
|---|---|---|
| Nontreated dogs at stage V (a or b) | 7 | 43 |
| Dogs at stage V (a or b) receiving chemotherapy | 36 | 93 |
| Nontreated dogs at stage V (a or b) with the bone marrow infiltrated at more than 30% | 4 | 4 |
| Dogs at stage V (a or b) with the bone marrow infiltrated at 30%, receiving chemotherapy | 21 | 30 |
| Dogs at stage V (a or b) receiving chemotherapy and vaccinated with the drug according to the invention (group 1) | >210 | >225 |
| Dogs at stage V (a or b) vaccinated with the drug according to the invention (group 2) | 160 | 208 |

Thus, for group 1 (immunotherapy according to the invention combined with chemotherapy), the data obtained are much more encouraging than those obtained in the literature without vaccination (median at 36 days and average at 93 days).

From a clinical point of view, the dogs in the group receiving the chemotherapy and the immunotherapy remain in complete remission throughout the experiment and those receiving the immunotherapy alone maintain a stable condition until the disease returns and requires them to be euthanized.

In total, the immunotherapy optionally combined with chemotherapy provides a significantly longer life expectancy than when it is not used. No side effect was observed.

Example 9

Effect of the Drug Combination According to the Invention in the Treatment of B Lymphomas in Dogs A study of the effect of the composition according to the invention on lymphomas was carried out on 50 dogs suffering from histologically established B lymphomas.

The dogs were typed according to WHO standards:

Stage I: involvement of one lymph node or one organ;

Stage II: regional involvement of several lymph nodes with or without the tonsils;

Stage III: polyadenomegaly;

Stage IV: liver and/or spleen involvement in addition to stages I to III;

Stage V: bone marrow and blood involvement in addition to stages I to IV.

The substages (a) equivalent to without clinical signs and (b) with clinical signs are also evaluated.

A lymph node is taken from a dog with a B lymphoma and the immunotherapy doses are prepared according to the protocol mentioned above with the process for preparing the composition and the vaccination kit (cf. examples 1 to 4)

A dose prepared according to example 2 is injected subcutaneously once a week for 4 weeks and then once a month for 4 months. 8 doses are therefore used. The vaccine is prepared from a surgical lymph node biopsy.

Three groups of dogs were formed:
a first group for which these doses were combined with a chemotherapy protocol including asparaginase, vincristine, adriblastine, cyclophosphamide, lomustine and prednisone, administered according to the protocol illustrated in FIG. 7,
a second group received the chemotherapy and only doses of placebo not containing autologous proteins (composition according to the invention).

At T0 and at the end of the treatment, an intradermal injection (0.1 ml) of autologous tumor extract was given in order to verify whether a delayed (48-72 h) hypersensitivity reaction occurred,
a third group received the vaccine doses alone.

Figure 6:
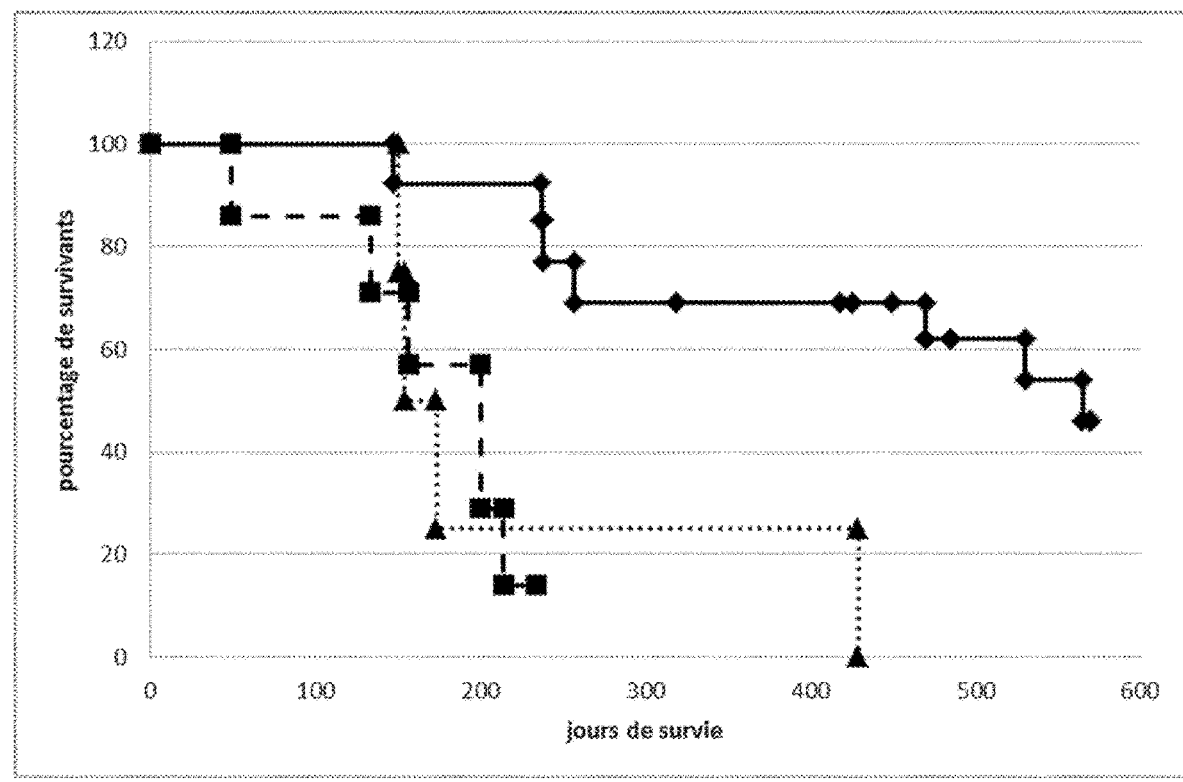
FIG. 6.

FIG. 6 illustrates the results of the study. There are three curves showing the survival in days and the percentage survival of dogs suffering from B lymphoma treated with the auto-vaccine according to the present invention alone (-▲-), dogs treated with the auto-vaccine according to the present invention in combination with a chemotherapy (-♦-) and dogs treated with a placebo in combination with a chemotherapy (-■-).

The survival curves show a survival that is very significantly increased when the dogs receive a treatment combining chemotherapy and immunotherapy (the composition according to the invention) compared with those receiving only the chemotherapy doses. The group receiving only immunotherapy has a survival comparable to that receiving the chemotherapy alone.

In total, the immunotherapy optionally combined with chemotherapy provides a significantly longer life expectancy than when it is not used. No side effect was observed.

These results suggest that this technique for stimulating the immune system is effective and could be of great advantage in humans in combination with a chemotherapeutic/radiotherapeutic treatment.

At the time of relapse, the dogs received an identical "emergency" chemotherapy. Three of them additionally benefited from a revaccination with vaccines prepared from the initial biopsy, while 4 other dogs benefited from a revaccination with a vaccine prepared from a new biopsy carried out during the relapse. The two groups had a longer survival than the dogs which received the emergency chemotherapy alone. The group of dogs vaccinated using the new biopsy survived for longer than those of the dogs vaccinated using the initial biopsy. It is therefore advantageous, at the time of relapse, to prepare a new vaccine from a new biopsy.

Example 10

Effect of the Use of the Composition According to the Invention in the Treatment of Melanoma in Horses Equine melanomas are much more frequent in gray and white horses than in horses which have a dark coat. Some breeds are particularly exposed, such as Camargue horses, which have a prevalence of close to 70% after 15 years.

The most common and most typical locations for these tumors are the ventral face of the tail (94% of cases in the Camargue horse), the perineum (43%) and the external genital organs.

A very interesting study by Seltenhammer et al. on 296 gray horses (Lipizzaners) showed that 148 of them manifested dermal melanomas (50%). Of the 68 over the age of 15, 51 had a melanoma. In 75% of cases, the melanomas were detected under the tail.

Several types of progression of these tumors can be distinguished:
- a slow growth over the course of numerous years (up to 20 years) without metastases;
- a slow growth over the course of several years, followed by a suddenly rapid growth and a malignant transformation;
- a rapid and malignant growth right from the start.

There is no real treatment for these tumors other than surgical resection, which is often difficult owing to their location, their multiple nature and their virtually systematic reappearance.

It is not possible to envision any chemotherapy in horses owing to the low nature of the benefit/risk ratio and the technical constraints that this would generate. The composition according to the invention as described The stimulation of the immune system against the abnormal proteins synthesized by tumor cells, by the composition according to the invention and as described in example 2, is an advantageous alternative, all the more so since it causes little or no side effects. Furthermore, the implementation is compatible with keeping the animal in its usual environment.

The abnormal proteins of the cancer cells of the melanoma of the horse were adsorbed onto a hydroxyapatite powder according to the technique described in example 2 (mineral vaccination adjuvant) with the kit described, this being in order to stimulate the immune system of the animal from which the cancer cells were isolated.

An ovoid-shaped tumor from the horse was chosen as a control since it was easily measurable.

The vaccine according to the invention consists of an injection of 0.5 ml of the composition (hydroxyapatite powder loaded with proteins specific for the horse's tumor) in the subcutaneous tissue every week for 1 month and every month for 4 months, which gives a total of 8 injections.

No side effect, neither local nor systemic, was noted, the horse having remained in the field throughout the treatment and having had a normal activity.

The volume of the tumor calculated from the measurements taken was reduced by 70% in a little less than 3 months.

This study shows that this treatment method according to the invention is effective on melanoma in horses and enables a regression of the tumor size. Total remission can be envisioned.

Example 11

Effect of the Reuse of the Composition During a Recurrence of B Lymphoma After Complete Remission On a series of 5 dogs which had, at varying times, suffered from a recurrence of their B lymphoma after a complete clinical and biological remission, manifesting itself through a reappearance of palpable lymph nodes and an enlargement of the tumors of various organs identified in the initial spread assessment or the reappearance of a medullary invasion, a treatment according to the invention was carried out again using an initial lymph node biopsy or a lymph node biopsy taken after the recurrence. Two groups were distinguished: a group having received chemotherapy plus a treatment according to the invention and treated again according to the invention after recurrence with the initial biopsy (I), a second group having received chemotherapy plus a treatment according to the invention and treated again according to the invention after recurrence with the second biopsy (post-recurrence) (II). The survival after recurrence of these two groups was compared with that of the placebo dogs treated with a further cycle of chemotherapy after recurrence (T). It appears that the survival of the two groups tested (I and II) is longer than that of the group T and that the survival of group II is longer than that of group I. It is therefore advantageous to treat again according to the invention after recurrence of the disease and, if possible, using a new biopsy.

Example 12

Synthesis of Gamma-Interferon by T Lymphocytes Stimulated by Dendritic Cells Activated In Vitro with the Powder Used According to the Invention The kit according to the invention was used to purify proteins from a tumor obtained by grafting of RT-4T1 cells on balb/c mice. Dendritic cells from these mice are obtained from macrophages cultured in the presence of IL-4 and of GM-CSF. At five days of culture, these cells are placed in the presence of variable amounts of solution for $10^6$ cells for 48 hours. These cells are then brought into contact with T lymphocytes from the same mouse line, and the gamma-interferon synthesized by these cells is assayed using an Elisa assay. Using 20 µl of solution of $10^6$ cells, there is a significant synthesis of gamma-interferon compared with the negative control.

The invention claimed is:

1. A method for treating B cell lymphomas in a subject comprising the step of administering to a subject suffering from B cell lymphomas an antitumor auto-vaccine composition, wherein the composition comprises a hydroxyapatite or tricalcium phosphate powder on which cytoplasmic proteins extracted from a tumor sample from said subject have been absorbed, said powder having a specific surface area SS≥m²/g and a particle size G≤200 µm, and being suspended in an injection liquid.

2. The method of claim 1, wherein the powder has undergone a sintering step between 400° C. and 600° C.

3. The method of claim 1, wherein the powder has a particle size G≤25 µm.

4. The method of claim 1, wherein the powder has a particle size G between 25 µm and 45 µm.

5. The method of claim 1, wherein the X-ray diffraction spectrum of the powder has a ratio of the width at half maximum to total height of the line, with an angle 2θ value equal to 31.773 degrees+/−1%, of between 0.2% and 0.35%.

6. The method of claim 1, wherein the subject is a human.

7. The method of claim 1, wherein the subject is a dog.

8. The method of claim 1, wherein the composition is administered in combination with an antitumor agent or a radiotherapeutic agent.

9. The method of claim 1, wherein one dose administered by injection to the subject comprises between 30 mg and 50 mg of hydroxyapatite or tricalcium phosphate and between 1000 µg and 2000 µg of proteins.

* * * * *